United States Patent [19]

Su et al.

[11] Patent Number: 5,276,192
[45] Date of Patent: Jan. 4, 1994

[54] PREPARATION OF PHENOXYETHANAMINES

[75] Inventors: Wei-Yang Su; George P. Speranza, both of Austin, Tex.

[73] Assignee: Texaco Chemical Company, White Plains, N.Y.

[21] Appl. No.: 689,388

[22] Filed: Apr. 22, 1991

[51] Int. Cl.$^5$ ............................................. C07C 217/14
[52] U.S. Cl. ...................... 564/354; 564/347; 564/353; 564/218; 564/219; 564/223; 548/237; 548/239
[58] Field of Search ............... 564/354, 359, 218, 219, 564/223; 548/237, 239

[56] References Cited

U.S. PATENT DOCUMENTS

| | | | |
|---|---|---|---|
| 3,654,229 | 4/1972 | Hunsucker | 260/67.6 R |
| 4,086,273 | 4/1978 | Berazosky et al. | 260/561 S |
| 4,195,154 | 3/1980 | Kaiser et al. | 528/98 |
| 4,234,743 | 11/1980 | Schulz et al. | 562/457 |
| 4,353,819 | 10/1982 | McFadden | 523/454 |
| 4,596,884 | 6/1986 | Maddig | 560/29 |

OTHER PUBLICATIONS

Snyder et al., JACS, 1953, 75, 2014–2015.
W. Seeliger, et al., "Recent Syntheses and Reactions of Cyclic Imidic Esters," Angew. Chem. internat. Edit., vol. 5, No. 10, 1966, pp. 875–888.
J. A. Frump, "Oxazolines. Their Preparation, Reactions, and Applications," Chemical Reviews, vol. 71, No. 5, 1971, pp. 483–499.
"Cyclic Imino Ethers, Polymerization," Encycl. Polym. Sci. Technol., Suppl. 1, 1976, pp. 220–237.
Chemical Abstracts 99(22):177867h, 1963.

*Primary Examiner*—Glennon H. Hollrah
*Assistant Examiner*—Shailendra Kumar
*Attorney, Agent, or Firm*—James L. Bailey; Kenneth R. Priem; David L. Mossman

[57] ABSTRACT

A process for preparing phenoxyethanamines from phenols and 2-oxazolines in quantitative yields was discovered. Phosphoric acid hydrolyzes the amide intermediate from the phenol/2-oxazoline reaction without cleaving the amide at the ether linkage and without undesired aromatic ring substitution. Thus, yield to the desired phenoxyethanamines is often 98% or better, requiring no subsequent purification. In contrast, sulfuric and hydrochloric acids give these undesired side reactions. Phenoxyethanamines are useful in thermosetting resins, pharmaceuticals and as surfactants.

4 Claims, No Drawings

PREPARATION OF PHENOXYETHANAMINES

FIELD OF THE INVENTION

The invention relates to a method for preparing phenoxyethanamines, and, in one aspect, more particularly relates to the preparation of phenoxyethanamines from amide intermediates using phosphoric acid.

BACKGROUND OF THE INVENTION

Phenoxyethanamines are known materials. They are useful, when at least partially neutralized, to produce thermosetting resins having extended pot life and a fast cure rate, such as described in U.S. Pat. No. 4,353,819, as an example. They have shown promise as surfactants as noted in Chemical Abstracts 99(22):177867h. Phenoxyethanamines are used to make froth-flotation collectors according to Chemical Abstracts 106(6): 36486j of European Patent Application 174,866, and in the production of coal flotation conditioners as described in Chemical Abstracts 103(18): 144675s of Indian patent document 154,360.

Unfortunately, phenoxyethanamines are difficult to make. While making the amide intermediates from reacting phenols with 2-oxazolines is known, converting them to the amines has proved hard. The sodium hydroxide method tends to have undesirably long reaction times. It was discovered herein that using hydrochloric acid or sulfuric acid to perform the hydrolysis gives poor selectivity to the desired phenoxyethanamine. Thus, it would be advantageous if a new route to these valuable materials were discovered.

J. A. Frump, in "Oxazolines. Their Preparation, Reactions, and Applications," Chemical Reviews, Vol. 71, No. 5, 1971, pp. 483–499 in his survey teaches the reaction of 2-phenyl-2-oxazoline and phenol over 7 hours to give N-[1-(2-phenoxyethyl)]benzamide. Other reactions with similar materials are also noted. Chemical Abstracts 99(22): 177867h, mentioned above, indicates that amines with the structure p—$C_9H_{19}C_6H_4O(CH_2CH_2O)_nCH_2CH_2NHR$, where R is hydrogen or $CO_2R^1$, $R^1$ being an alkyl having 1 to 5 carbon atoms, and n is 0 to 10, are prepared by treating p—$C_9H_{19}C_6H_4O(CH_2CH_2O)_nH$ with $CH_2=CHCONHR$, where R is defined as above, in the presence of polymerization inhibitors and then converting the amide intermediate to the amine by a Hofmann rearrangement.

An improved vehicle for the formulation of baking enamels may be obtained by reacting an oxazoline with phenol according to U.S. Pat. No. 3,654,229. Materials such as 2-[1,1-bis(hydroxymethyl)] oxazoline diester and 2-[1,1-bis(hydroxymethyl)ethyl]-4-ethyl-4-propionoxymethyl-2-oxazoline were reacted with phenol. The products were dissolved in methanol to form the vehicles.

U.S. Pat. No. 4,596,884 describes an improved process for the preparation of 5-ethyl-4-(2-phenoxyethyl)-1,2,4-triazolone, a useful intermediate in the synthesis of antidepressant 1,2,4-triazolones. One of the steps in the process involves the reaction of phenol and 2-ethyl-2-oxazoline to give an intermediate compound N-(2-phenoxyethyl)propionamide. The reactions of cyclic imidic esters (2-oxazolines) with phenols and other materials proceed with ring cleavage and formation of 2- or 3-substituted N-alkylamide derivatives, and less frequently of 2-aminoethyl or 3-aminopropyl esters of carboxylic acids, as taught by W. Seeliger, et al., "Recent Syntheses and Reactions of Cyclic Imidic Esters," Angew. Chem. internat. Edit., Vol. 5, No. 10, 1966, pp. 875–888.

U.S. Pat. No. 4,195,154 describes the preparation of 2-amido- or 2-amino-alkyl ethers of polyhydric polyphenols by reacting a 2-oxazoline with a polyhydric polyphenol in the presence of certain metal salt catalysts, e.g. zinc acetate. The resulting materials appear to have use as epoxy curing agents and have insecticidal, fungicidal and bacteriocidal activity.

Of lesser importance and relating to the background of 2-oxazolines, is the article "Cyclic Imino Ethers, Polymerization" appearing in Encycl. Polym. Sci. Technol., Suppl. 1, 1976, pp. 220–237. Somewhat similar reactions to those described above are seen in U.S. Pat. No. 4,086,273 which reacts n-octylmercaptan with 2-ethyl-2-oxazoline in the presence of a catalytic amount of hydrated cadmium chloride at a temperature of approximately 200° C. for one hour. The resulting β-aminoethyl sulfides are known to have a variety of uses.

SUMMARY OF THE INVENTION

Accordingly, it is an object of the present invention to provide a process for the production of phenoxyethanamines that does not require extraordinarily long reaction times.

It is another object of the present invention to provide a process for the preparation of phenoxyethanamines having a better selectivity to the desired products, as compared with other processes.

Another object of the invention is to provide a simple method for production of phenoxyethanamines having uses as surfactants.

In carrying out these and other objects of the invention, there is provided, in one form, a process for producing a phenoxyethanamine by a first step of reacting a phenol with a 2-oxazoline to produce an amide intermediate. The second step involves hydrolyzing the amide intermediate with phosphoric acid to give the phenoxyethanamine.

DETAILED DESCRIPTION OF THE INVENTION

It has been found that phenoxyethanamines may be made from phenols (I) and 2-oxazolines (II) according to a two-step process. Phosphoric acid has been discovered to be an excellent proton source for hydrolyzing the amide intermediates (III) to the phenoxyethanamines (IV). In fact, using the method of this invention, yields to the phenoxyethanamines regularly exceed 95%, usually 98% and even 99%. The two-step process may be schematically represented as follows:

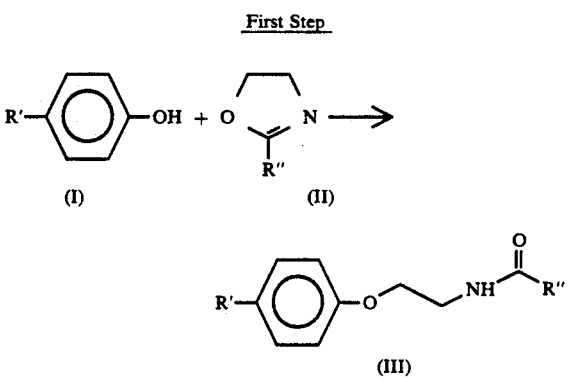

Second Step

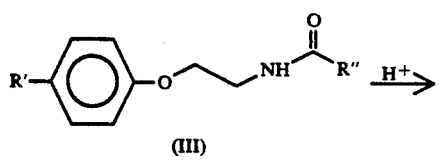

(III)

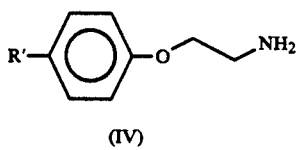

(IV)

As noted above, the phenols (I) useful in the process of the present invention may have the formula:

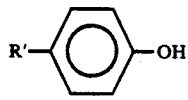

where is R' selected from the group consisting of hydrogen, alkyl, aryl, alkoxy, aryloxy, alkaryloxy, and halogenated aryl, having 1 to 18 carbon atoms. Most broadly, R' may be any moiety that does not interfere with the reactions. For example, the group should not be acidic, such as the acidic proton on a hydroxyl group: —OH. Representative, though non-limiting examples of phenols that are suitable and which fall within this definition include phenol, nonylphenol and bisphenol A.

The 2-oxazolines (II) suitable for the process herein may have the formula:

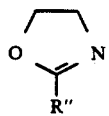

where R" may be hydrogen, a straight or branched alkyl group of 1 to 18 carbon atoms. Appropriate oxazolines include, but are not limited to 2-methyl-2-oxazoline and 2-ethyl-2-oxazoline.

Surprisingly, hydrolysis of the amide intermediates (III) having the formula:

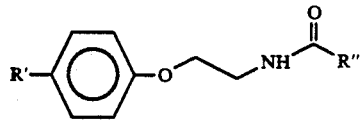

where R' and R" are defined as above, in the presence of phosphoric acid does not cause cleavage at the ether oxygen or aromatic ring substitution. These undesirable side reactions occur with other acids such as hydrochloric and sulfuric, and thus selectivity to the desired phenoxyethanamines (IV):

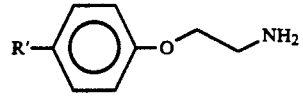

is poor. Indeed, by using phosphoric acid, high purity products are obtained which surprisingly do not need further purification. The method of this invention is also considerably shorter than the hydrolysis using sodium hydroxide. For example, the NaOH method requires on the order of 120 hours, whereas the inventive process takes about 4 to 8 hours or so. The method of this invention is a superior way to make simple SURFON-AMINE ® amines, sold by Texaco Chemical Company.

Both steps of this invention may be conducted at atmospheric pressure. The temperature range for the first step may be in the range from about 100° to about 300° C., preferably from about 140° to about 220° C. The temperature range for the second step may be in the range from about 60° to about 200° C., preferably from about 100° to about 150° C. No catalyst is required for either step of this invention, although one may be yet discovered which might facilitate the phenoxyethanamine preparation.

The invention will be further illustrated by the following examples which are provided for further understanding and not to limit the scope of the invention.

EXAMPLE 1

Preparation of N-[1-(2-phenoxyethyl)]acetamide Intermediate

To a 500-ml three-necked flask equipped with a thermometer, stirrer, condenser and nitrogen inlet were charged 144.5 g. of 2-methyl-2-oxazoline and 159.8 g. of phenol. The mixture was heated to 160° C. for six hours. The resulting solid product was recrystallized from water to give N-[1-(2-phenoxyethyl)]acetamide intermediate as white, needle crystals with a melting point of 87° C.

EXAMPLE 2

Preparation of 2-phenoxyethanamine Using Phosphoric Acid

To a 250-ml three-necked flask equipped with a thermometer, stirrer, condenser and nitrogen inlet were charged 20 g. of N-[1-(2-phenoxyethyl)]acetamide intermediate from Example 1, 30 g. of 85% phosphoric acid and 10 g. of water. The mixture was heated to reflux for eight hours. The resulting reaction mixture was neutralized with sodium hydroxide solution and extracted with toluene. The toluene was then removed at reduced pressure. About 15.1 g. of 2-phenoxyethanamine was obtained (98% yield). The nature of the product was confirmed by NMR spectroscopy.

EXAMPLE 3

Preparation of 2-Phenoxyethanamine Using Sulfuric Acid

The procedure of Example 2 was followed except that 100 g. of 60% sulfuric acid (in place of phosphoric acid) and 20 g. of the phenoxyethylacetamide intermediate were employed. About 1 g. of 2-phenoxyethanamine along with 13.3 g. of the corresponding sulfonate were obtained. This example demonstrates that sulfuric acid is not suitable for this process; poor selectivity to the desired phenoxyethanamine results due primarily to aromatic ring substitution.

EXAMPLE 4

Preparation of 2-Nonylphenoxyethanamine Using Phosphoric Acid

To a 250-ml three-necked flask equipped with a thermometer, stirrer, condenser and nitrogen inlet were charged 66 g. of nonylphenol and 30 g. of 2-methyl-2-oxazoline. The mixture was heated to 200° C. for six hours. About 80 g. of 85% phosphoric acid and 20 g. of water were then added. The mixture was heated to reflux for eight hours. The resulting reaction mixture was neutralized with sodium hydroxide solution. The resulting product was washed with water and then dried. 2-Nonylphenoxyethanamine was obtained in quantitative yield and the product purity by NMR spectroscopy analysis was found to be about 98%.

EXAMPLE 5

Preparation of 2-Nonylphenoxyethanamine Using Sulfuric Acid

The procedure of Example 4 was followed except that sulfuric acid was used in place of the phosphoric acid. NMR spectroscopy analysis showed that the product contained about 10% sulfonate derivatives. Thus, the yield to the desired phenoxyethanamine was 90% at most.

It should be noted that there are a number of possible by-products when ether cleavage and/or ring substitution occurs and that many of the by-products are similar in boiling point to the desired phenoxyethanamines, making separations difficult.

EXAMPLE 6

Preparation of Bisphenol A Diaminoethyl Ether

To a 500-ml three-necked flask equipped with a thermometer, stirrer, condenser and nitrogen inlet were charged 60 g. of bisphenol A and 52 g. of 2-methyl-2-oxazoline. The mixture was heated to 200° C. for six hours. About 130 g. of 85% phosphoric acid and 40 g. of water were then added. The mixture was next heated to reflux for eight hours. The resulting reaction mixture was neutralized with sodium hydroxide solution. The resulting product was washed with water and then dried. Bisphenol A di-2-aminoethylether was obtained in quantitative yield and the product purity by NMR spectroscopy analysis was about 99%.

It will be appreciated that the yields to the phenoxyethanamines are excellent, even though the process is not necessarily optimized. Many modifications may be made in the process of this invention without departing from the spirit and scope thereof which are defined only in the appended claims. For example, one skilled in the art may discover that certain reaction conditions may give particularly advantageous results.

I claim:

1. A process for producing a phenoxyethanamine comprising the steps of:
   reacting a phenol with a 2-oxazoline to produce an amide ether intermediate; and
   hydrolyzing the amide ether intermediate with water in the presence of phosphoric acid catalyst to give the phenoxyethanamine.

2. The process of claim 1 where the phenol has the formula:

where R' is selected from the group consisting of hydrogen, alkyl, aryl, alkoxy, aryloxy, alkaryloxy, and halogenated aryl, having 1 to 18 carbon atoms.

3. The process of claim 1 where the 2-oxazoline has the formula:

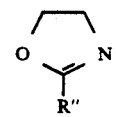

where R" may be hydrogen, a straight or branched alkyl group of 1 to 18 carbon atoms.

4. A process for producing a phenoxyethanamine of the formula

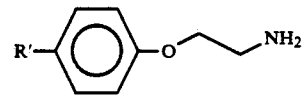

where R' is selected from the group consisting of hydrogen, alkyl, aryl, alkoxy, aryloxy, alkaryloxy, and halogenated aryl, having 1 to 18 carbon atoms, comprising the steps of:
   reacting a phenol of the formula:

with a 2-oxazoline of the formula:

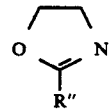

where R" may be hydrogen, a straight or branched alkyl group of 1 to 18 carbon atoms, to produce an amide ether intermediate; and
   hydrolyzing the amide ether intermediate with water in the presence of phosphoric acid catalyst to give the phenoxyethanamine.

* * * * *